United States Patent
Zanette et al.

(10) Patent No.: US 6,573,366 B1
(45) Date of Patent: Jun. 3, 2003

(54) **PROCESS FOR THE PURIFICATION OF HUMAN INTERLEUKIN-1 RECEPTOR ANTAGONIST FROM RECOMBINANT *E. COLI***

(75) Inventors: Dino Zanette, Pianzano Godega S. Urbano (IT); Edoardo Giacomo Sarubbi, Fontenay sous Bois (FR); Adolfo Soffientini, Sesto S. Giovanni (IT)

(73) Assignee: Gruppo Lepetit S.p.A., Milan (IT)

( * ) Notice: Subject to any disclaimer, the term of this patent is extended or adjusted under 35 U.S.C. 154(b) by 0 days.

(21) Appl. No.: 09/568,202

(22) Filed: May 9, 2000

Related U.S. Application Data

(63) Continuation of application No. 09/194,645, filed on Mar. 29, 1999, now abandoned.

(30) Foreign Application Priority Data

Jun. 7, 1996 (GB) .............................................. 96109153

(51) Int. Cl.$^7$ .............................. C12P 21/00; C07K 1/00
(52) U.S. Cl. ..................... 530/416; 435/69.1; 435/69.5; 435/71.1; 514/2; 530/412; 530/350; 530/351
(58) Field of Search ................................. 530/350, 351, 530/412, 416; 435/69.1, 69.5, 71.1; 514/2

(56) References Cited

FOREIGN PATENT DOCUMENTS

EP   WO 96/09323   *   3/1996

OTHER PUBLICATIONS

Atkinson, B and Mavituna, F. Biochemical Engineering and Biotechnology Handbook, Macmillian Publishers Ltd, New York, 1991, p. 1009.*
Frej, A. et al., Biotechnology and Bioengineering, 44(922–929) Jul. 1994.*

* cited by examiner

*Primary Examiner*—Yvonne Eyler
*Assistant Examiner*—Michael Brannock
(74) *Attorney, Agent, or Firm*—George G. Wang

(57) ABSTRACT

A process for purifying human Interleukin-1 receptor antagonist (IL-1ra), obtained by fermenting a strain of recombinant *E. coli*, which comprises: a) loading the mixture to be purified, which has been buffered at a pH value lower than 6.2 and optionally diluted to reduce its ionic strength at a low value, onto a cationic exchange matrix and eluting said matrix with an aqueous buffered solution having a pH value from about 7.5 to 9.0 and a low ionic strength; and b) applying the eluate from the cationic exchange step, containing the desired IL-1ra protein, directly onto an anionic exchange matrix and eluting with an aqueous buffered solution having a pH value within the above range 7.5 to 9.0 and an increased ionic strength.

17 Claims, No Drawings

PROCESS FOR THE PURIFICATION OF HUMAN INTERLEUKIN-1 RECEPTOR ANTAGONIST FROM RECOMBINANT E. COLI

This is a continuation of Ser. No. 09/194,645 filed Mar. 29, 1999, abandoned, which is a 371 of PCT/EP97/02591 filed May 21, 1997.

The present invention refers to a new purification process of the human Interleukin-1 receptor-antagonist (IL-1ra) obtained by fermenting a strain of recombinant E. coli.

As known, the members of the interieukin-1 (IL-1) family are important mediators of inflammatory, and immune responses. Among these Interleukin-1α and β (IL-1α and IL-1β) behave as agonists on the IL-1 receptors, being responsible for the stimulation of a number of cellular activities related to inflammatory and immune responses.

IL-1ra (the third member of the IL-1 family) is a protein that, like IL-1α and IL-1β, binds both the IL-1receptor type I (IL-1R type I) on the T-cells (see Cannon J. H. et al., J. Infect. Dis., 1990, 161, 79 and Hannum C. H. et al., Nature, 1990, 343, 336) and the IL-1R type II on polymorphonuclear leukocytes and and B-cells (see Grarowitz E. V. et al., J. Biol. Chem., 991, 266, 14147 and Dripps D. J. et al., J. Biol. Chem., 991, 266, 20311). Nevertheless, differently from IL-1α and IL-1β, IL-1ra acts as a pure antagonist, blocking the binding of the IL-1α and IL-1β proteins to the said receptor and thereby providing a relevant control of on the whole IL-1 system.

Although extremely important for mediating the immunological response against pathogens, overproduction of IL-1(i.e. IL-1α and IL-1β) may in some cases lead to undesired pathogenic conditions. This is, for instance, the case of septic shock, graft versus host disease or autoimmune diseases, such as rheumatoid arthritis, insulin-dependent diabetes mellitus, multiple sclerosis and certain types of leukemia.

As showed by a number of authors, the inhibition of the IL-1 activity by IL-1ra in said pathogenic conditions could have therapeutic effects (see for instance, Dinarello C. A., Adv. Pharmacol., 1994, 25, p. 21 and Dower K. S. et al., Therap. Immunol., 1994, 1, p. 113). It appears however that relatively high amounts of protein are required in order to achieve significant clinical results (Fisher C. J. et al., JAMA, 1994, 271, 1836).

Because of the evident difficulties of providing high amounts of the human IL-1ra for further studies, the preparation of recombinant IL-1ra proteins is highly desirable.

The IL-1ra protein produced by recombinant E. coli according to the present fermentation process is an ungly-cosylated protein of about 17.5 kDa which has an affinity for the IL-1R type I similar to the one of the natural occurring glycosylated protein (Molecular weight of about 22 kDa), as disclosed by Schreuder et al., Eur. Jour. Biochem., 227, 838–847, (1995). Furthermore, it has been shown that said recombinant IL-1ra inhibits a variety of IL-1 dependent processes both in vitro (see Eisenberg S. P. et al., Nature, 1990, 343, 341; Arend W. P. et al., J. Clin. Invest., 1990, 85, 1694 and McIntyre K. W. et al., J. Exp. Med., 1991, 73, 931) and in vivo (see Rambaldi A. Et al., Blood, 1990, 76, 114; Cominelli F. et al., J. Clin. Invest., 1991, 86, 972 and Alexander H. R. et al., J. Exp. Med., 1991, 173, 1029).

The expression of the recombinant IL-1ra and its purification from the fermentation broth are disclosed by Schreuder et al., Eur. Jour. Biochem., 227, 839–847 (1995). Briefly, a IL-1ra producing recombinant Escherichia coli is prepared by inserting the human IL-1ra gene (from BBL—British Biotechnology Labs) into the TAC-Bsp vector by cutting the BBL IL-1ra vector with HindIII and BamHI, isolating the HindIII-BamHI fragment and inserting this latter into a BspMI/BamHI-digested TAC-Bsp vector with the addition of two linker oligonucleotides to bridge the restriction site and to put the gene in frame.

The so obtained recombinant E. coli is grown overnight at 37° C. in Luria broth containing 50 μg/ml of ampicillin; bacterial cells are then harvested by centrifugation and stored at −80° C. until use.

According to the recovery procedure disclosed in the above document, bacterial cells are then lysed by sonication, centrifuged and clarified to remove cell debris.

For purification purposes, the clarified suspension is first passed through a hydrophobic interaction matrix (Phenyl-sepharose Fast-Flow, Pharmacia) using a salt-gradient elution; fractions containing the IL-1ra are pooled, dialyzed and passed through an anionic matrix (MonoQ with FPLC system, Pharmacia), then ammonium sulfate is added to the fractions containing the IL-1ra which are again passed through the hydrophobic interaction matrix and finally purified by gel filtration.

According to other purification, procedures, the recombinant IL-1ra protein contained in the clarified solution may also be purified by using two anionic exchange matrices and a size exclusion chromatography, as disclosed by D. B. Carter et al., Nature, 344 (19901), pp. 633–638, or by employing an anionic exchange chromatography, an hydrophobic interaction chromatography and a size exclusion chromatography, as disclosed by O. M. P. Singh et al., Spec. Publ.—R. Soc. Chem. (1994), 158 (Separations for Biotechnology 3), pp. 474–481.

It has now been found that the purification of IL-1ra protein can be easily achieved by using a simple two-step purification process which employs a cation exchange matrix and an anion exchange matrix.

In particular, the first elution is achieved by increasing the pH of the eluent with respect to the one of the loading mixture. The eluates containing the IL-1ra protein from the first chromatographic column are then directly loaded onto the second chromatographic column, without any intermediate operation such as diafiltration or dialysis; the second elution is then achieved by increasing the ionic strength of the eluent with respect to the one of the mixture eluted from the first chromatographic step.

As the skilled man will appreciate, the present purification method can be applied, using a conventional chromatographic system, to the clarified suspension obtained by the fermentation process described above, after treatment of the recombinant E. coli fermentation mass.

However, according to a preferred embodiment, the first purification step onto the cationic exchange matrix is preferably performed under the conditions of the so-called "expanded bed adsorption technique". This technique, based upon fluidization, relies on the use of particular columns and ion exchangers, which allow to feed the column with a crude feed, without the need of preliminary operations for cell debris removal, such as concentration and/or clarification. Whilst the desired protein is adsorbed onto the matrix, the cell debris passes through the column unhindered and is then discarded (together with the unbound proteins). Accordingly, the homogenate obtained after cell disruption does not need to be clarified and filtered, as disclosed in the above prior art documents for eliminating the cell debris, but may directly be loaded onto the first cationic exchange matrix (see Hjorth et al., Bioseparation, 5(4), 217–223, 1995).

By coupling the expanded bed adsorption technique with the improved two-step chromatographic purification, a new simple procedure for the purification of IL-1ra from recombinant *E. coli* is thus provided; as a further advantage, in view of the low number of operations, the present purification process is also easily scalable for an industrial production of the IT-1ra recombinant protein.

As a general procedure, the cationic exchange matrix is first swallen by addition, of a suitable aqueous buffered solution (buffer A) having a pH lower than 6.2, preferably from about 5.0 to about 6.2, particularly preferred being a pH of about 6.0. For instance, buffered solutions containing MES (4-morpholineethanesulfonic acid), BIS-TRIS (2-bis (2-hydroxyethyl)amino-2-(hydroxymethyl)-1,3-propandiol) or citrate may be employed. If desired, further compounds may be added to the buffering solution, for instance protease inhibitors such as EDTA (ethylendiamino-tetraacetic acid) or PMSF (benzenemethanesulfonyl fluoride). A suitable buffering solution may be prepared, for instance, with 20 mM MES and 1 mM EDTA (pH about 6.0). The column is then loaded with the mixture to be purified, which will be either a clarified solution when a conventional chromatographic technique is applied or an homogenate containing the cell debris when the expanded bed adsorption technique is applied. The mixture to be purified is loaded as a solution with a buffer having a pH value within the above range (lower than 6.2, preferably 5.0–6.2), the buffer solution being preferably the one employed for the expansion of the matrix. The addition of the buffered solution has also the result of diluting the mixture to be purifed, so to achieve a low ionic strength of the loading solution; if necessary, the ionic strength of the loading mixture may be further lowered by diluting it with deminerilazed water.

Before eluting, the column is washed with a suitable buffer, preferably with the same buffer A used for expanding the matrix; preferably, after washing with buffer A, the column is then washed with water, so to minimize undesired pH's gradients inside the column.

The IL-1ra protein is then eluted with another aqueous buffered solution buffer B), having a pH value of from about 7.5 to about 9.0, preferably about 8.0. For instance, buffered solutions containing TRIS (2-amino-2-(hydroxymethyl)-1, 3-propanediol), HEPES (4-(2-hydroxy-ethyl)-1-piperazineethanesulfonic acid) or phosphate may be employed. Also in this case, as for buffer A, suitable additives may be added to the buffered solution. A suitable buffering solution may be prepared, for instance, with 25 mM TRIS and 1 mM EDTA (pH about 8.0).

The monitoring of the eluates is performed according to the known techniques, such as by UV analysis.

By following the above procedure, the eluted solution containing the desired IL-1ra, which will have a pH value within the range above defined for buffer B (i.e. 7.5 to 9.0) and a low ionic strength, may directly be loaded onto the anionic exchange resin.

The eluates from the cationic exchange column, containing the desired IL-1ra protein, are thus directly loaded onto the anionic exchange matrix, which has been previously equilibrated with a suitable buffer, preferably with the same buffer B used for eluting the IL-1ra protein from the cationic exchange matrix. After washing the loaded matrix, preferably with buffer B, the IL-1ra protein is then eluted with an aqueous buffered solution (buffer C) having the same pH as buffer B (i.e. from about 7.5 to 9.0, preferably about 8.0) but with an increased ionic strength (measured as conductivity of the solution).

As a general indication, the buffer B solution, which should have a low ionic strength, will in general have a conductivity lower than 3.0 mS/cm$^2$, preferably lower than 1.5 mS/cm$^2$, particularly preferred being a conductivity of about 0.9–1.0 mS/cm$^2$. As said above, also the ionic strength of the mixtures loaded onto the ionic exchange matrices should be kept at low values; thus the above conductivity values are also desirable for these mixtures. On the other side, the buffer C solution, which has an increased salt content will in general have a conductivity higher than 9 mS/cm$^2$, preferably from 9 to 15 mS/cm$^2$, particularly preferred being a conductivity of about 10 mS/cm$^2$.

As known in the art, for increasing the ionic strength of a buffered solution, a non-buffering salt is added thereto, such as NaCl, KCl and the like. Buffering agents and additives for buffer C are generally the sable as those employed for buffer B. For instance, a suitable solution for buffer C may be prepared with 25 mM TRIS, 100 mM NaCl and 1 mM EDNA (pH about 8.0, conductivity about 10 mS/cm$^2$).

Also in this case, the monitoring of the eluates is performed according to the known techniques, such as by UV analysis.

At the end of the chromatographic purification, the obtained solution is then treated as known in the art for recovering the pure IL-1ra recombinant protein. For instance, tipical operations which may be applied, also in combination, for recovering the pure product are concentration, filtration and diafiltration.

When conventional ion exchange chromatographic techniques are employed, suitable cationic exchangers which may be employed in the first chromatographic step are the conventional cellulose based, dextran based, agarose or cross-linked agarose based, synthetic organic polymers based, coated silica matrices based cation exchangers, which may be functionalized with carboxymethyl, sulfonate, sulfoethyl or sulfopropyl groups. Preferably, cross-linked agarose based or synthetic organic polymers based cation exchangers are employed, which are preferably functionalized with sulfonate or sulfopropyl groups.

Examples of commercially available cationic exchangers are the cellulose based CM 23, CM 32 and CM 52 (Whatman); the dextran based CM-Sephadex C-25, SP-Sephadex C-25, CM-Sephadex C-50 and SP-Sephadex C-50 (Pharmacia); the agarose or cross-linked agarose based CM Bio-gel A (Biorad), CM-Sepharose CL-6B and S-Sepharose Fast Flow (Pharmacia); the synthetic organic polymer based Mono S (Pharmacia), S-Hyper D (Biosepra), SP-5-PW and HRLC MA7C (Biorad) and the and the coated silica matrices based such as CM Si300 and SP Si100 (Serva). Preferred matrices are S-Sepharose, Mono S and S-Hyper D.

According to the preferred embodiment, when the "expanded bed adscrption technique" is applied in the first chromatographic step, a particular column and ion exchanger are employed. In the specific, the column is provided with a mobile top adaptor, moved by hydraulic drive, and with a net at the top and the bottom of it, which permits the passage of the cell debris but not of the bead particles of the ion exchanger. The ion exchanger matrix is formed by special beads which are made heavier with respect to the beads employed in the conventional technique. The ion exchange matrix may be selected from the above cited cation exchange matrices, i.e. cellulose based, dextran based, agarose or cross-linked agarose based, synthetic organic polymers based, functionalized with carboxymethyl, sulfonate, sulfoethyl or sulfopropyl groups; said matrices are made heavier with respect to conventional matrices by addition of inert material to the beads, for instance quarz.

Preferably, cross-linked agarose based cation exchangers are employed, which are preferably functionalized with sulfonate or sulfopropyl groups.

For instance, a STREAMLINE column (Pharmacia) filled with the a modified cross-linked agarose based cationic exchanger such as SP-STREAMLINE (modified SP-Sephadex, Pharmacia) can conveniently be employed.

Suitable anionic exchangers which may be employed in the second chromatographic step are the cellulose based, dextran based, agarose or cross-linked agarose based, synthetic organic polymers based and coated silica matrices based anion exchangers, which may be functionalized with diethylaminoethyl, quaternary aminomethyl, quaternary aminoethyl diethyl-(2-hydroxypropyl)aminoethyl, triethylaminbmethyl, triethylaminopropyl and poliethyleneimine groups. Preferably, cross-linked agarose based or synthetic organic polymers based anion exchangers are employed, which are preferably functionalized with a quaternary aminomethyl group.

Examples of commercially available anionic exchangers are the cellulose ion exchangers such as DE 32 and DE 52 (Whatman), the dextran ion exchangers such as DEAE-Sephadex C-25, QAE-Sephadex C-25, DEAE-Sephadex C-50 and QAE-Sephadex C-50 (Pharmacia), the agarose or cross-linked agarose such as DEAE Bio-gel A (Biorad), DEAE-Sepharose CL-6B and Q-Sepharose Fast Flow (Pharmacia), the synthetic organic polymers, such as Mono Q (pharmacia), Q-Hyper D (Biosepra), DEAE-5-PW and HRLC MA7P (Biorad) and the coated silica matrices such as DEAE Si5500 and TEAP Si100 (Serva). Preferred matrices are Q-Sepharose, Mono Q and Q-Hyper D; preferably the Q-Sepharose is employed as the anionic exchanger.

The following examples illustrate more in detail the purification process of the present invention.

Buffered solutions

| Buffer | Composition | pH | Conductivity (mS/cm$^2$) |
|---|---|---|---|
| A | 20 mM MES, 1 mM EDTA | 6.0 | ≈0.9–1.0 |
| B | 25 mM TRIS, 1 mM EDTA | 8.0 | ≈0.9–1.0 |
| C | 25 mM TRIS, 100 mM NaCl, 1 mM EDTA | 8.0 | ≈10 |
| D | 25 mM TRIS, 1 M NaCl, 1 mM EDTA | 8.0 | ≈78 |
| E | 50 mM Na$_2$HPO$_4$, 150 mM NaCl | 7.3 | n.e. | n.e. = not evaluated

EXAMPLE 1

Fermentation of Recombinant *E. coli*

Recombinant *E. coli* K12 (AB1899) containing the plasmid for the expression of IL-1ra is grown in a 50 liters fermenter overnight at 37° C. in Luria broth containing 50 μg/ml of amplicillin, as described by Schreuder et al., Eur. Jour. Biochem., 227, 838–847 (1995).

EXAMPLE 2

Cell Harvesting

At the end of the fermentation process, 50 l of fermentation broth are discharged and the cells are harvested with the FC-5B refrigerated superspeed centrifuge (SORVALL) with the TZ 28 zonal rotor (SORVALL) at a loading flow rate of 12 l/h. About 350 g of cell paste are harvested, divided into aliquotes and stored at −80° C.

EXAMPLE 3

Cell Washing and Harvesting 250 g of cell paste from Example 2 are thawed. The cell paste is suspended in Buffer A (about 15 ml/g of cell paste). This suspension is passed through a DYNO-MILL apparatus (WAB AG, Basel) in a continuous manner at a flow rate of about 5 l/h, in order to dasrupt the cells. The cell disruption is controlled with the microscope. The volume of the homogenate is then brought to about 5600 ml with Buffer A, so that the conductivity is between 900–1000 mS/cm$^2$ and that the pH value is about 6.0.

EXAMPLE 4

First Ion Exchange Step (Expanded Bed Principle)

Chromatographic system: STREAMLINE (Pharmacia):
   50×1000 mm STREAMLINE glass column filled with 600 ml of SP-STREAMLINE cation exchanger;
UV detection: UVICORD S1 Monitor+Industrial cell (Pharmacia LKB); recorder Rec 102 (Pharmacia); γ=280 nm
Flow Rates: expansion, loading 4800 ml/h
   washing, packing, elutior 1100 ml/h Since his first step is based on the expanded bed adsorption principle, there is no need to clarify and filter the homogenate obtained according to Example 3. The matrix is first expanded with Buffer A (pH 6.0) to about 2.5 times the volume of the matrix when it is packed. The homogenate from Example 3 (containing also the cell debris) is loaded directly onto the ion exchange matrix from the bottom of the column. The column is thoroughly washed with Buffer A to remove all of the debris and then with water to remove Buffer A; finally, the cationic exchange matrix is packed by hydraulicly lowering the top adaptor of the column. Once the matrix is packed, IL-1ra is eluted with Buffer B, by reversing the flow direction (i.e. from the top to the bottom of the column).

This type of elution allows to directly load the eluate obtained from the SP-Streamline ion exchanger onto the second ion exchange matrix, without the need to concentrate and diafiltrate this eluate.

EXAMPLE 5

Second Ion Exchange Step

Chromatographic system: Biopilot (Pharmacia):
   50–300 mm glass column filled with 200 ml of Q-Sepharose FF anion exchanger;
UV detection at λ=280 nm
Flow Rates: equilibrating, loading, washing 1000 ml/h
   elution 2000 ml/h The Q-Sepharose containing column is equilibrated with Buffer B. The eluate obtained from the SP-Streamline is loaded directly onto this second matrix. The matrix is then washed with Buffer B. Once the adsorbance returns to the baseline, IL-1ra is eluted with Buffer C, collecting about 400 ml of eluate containing the IL-1ra recombinant protein.

To eliminate impurities tightly bound to the matrix, the column is finally washed with Buffer D.

EXAMPLE 6

Concentration and Diafiltration

The eluate from the second chromatography is concentrated using S1 YM3 membranes (AMICON). After having reduced the initial eluate volume 10 fold, the concentrate is diafilterd with Buffer B, monitoring the pH and the conductivity of the filtered solution.

At the end of the purification process, about 1.5 g of IL-1ra recombinant protein are recovered, with a purity higher than 95%, as determined by SDS-PAGE analysis (Pharmacia LKB—PHAST SYSTEM; PHAST Gel SDS-PAGE 8–25%).

What is claimed is:

1. A process for purifying human Interleukin-1 receptor antagonist (IL-1 ra) from a mixture made from a strain of recombinant *E. coli*, which comprises:
   a) loading the mixture, which has been buffered at a pH value lower than 6.2 and optionally diluted to reduce its ionic strength to a conductivity value lower than 3.0 mS/cm$^2$, onto a cationic exchange matrix and eluting with an aqueous buffered solution having a pH value from about 7.5 to 9.0 and an ionic strength such that the conductivity value is lower than 3.0 mS/cm$^2$ to obtain an eluate;
   b) applying the eluate directly onto an anionic exchange matrix and eluting with an aqueous buffered solution having a pH value of about 7.5 to 9.0 and an ionic strength such that the conductivity value Is higher than 9 mS/cm$^2$ to obtain a second aluate; and
   c) recovering IL-1ra from the second equates.

2. A process according to claim 1 wherein step (a) is performed according to the expanded bed adsorption technique, which comprises loading a cell debris containing homogenate onto the cationic exchange matrix, said homogenate being obtained directly from the fermentation mass by cell harvesting, washing and disruption, without subsequent clarification and filtration.

3. A process according to claim 1 wherein the cationic exchange matrix is first expanded with an aqueous buffered solution having a pH value lower than 6.2.

4. A process according to claim 3 wherein, after applying the mixture to be purified onto the cationic exchange matrix and before eluting it, said matrix is first washed with the same buffer used for its expansion and then optionally with water.

5. A process according to claim 4 wherein the pH of the aqueous buffered solution used for expanding the cationic exchange matrix and for its washing and the pH of the mixture to be loaded onto the cationic exchange matrix is from about 5.0 to about 6.2.

6. A process according to claim 1 wherein the pH of the aqueous buffered solution employed for eluting the cationic exchange matrix and of the aqueous buffered solution employed for eluting the anionic exchange matrix is about 8.0.

7. A process according to claim 1 wherein the conductivity of the mixture loaded onto the cationic exchange matrix, of the aqueous buffered solution used in step(a) and of the eluate loaded onto anionic exchange matrix is lower than 1.5 mS/cm$^2$.

8. A process according to claim 1 wherein the conductivity in step (a) is about 0.9–1.0 mS/cm$^2$.

9. A process according to claim 1 wherein the conductivity of the aqueous buffered solution employed for eluting the anionic exchange matrix is between 9.0 and 15.0 mS/cm$^2$.

10. A process according to claim 9 wherein the conductivity of the aqueous buffered solution employed for eluting the anionic exchange matrix is about 10.0 mS/cm$^2$.

11. A process according to claim 4 wherein the aqueous buffered solution for expanding the cation exchange matrix, for buffering the mixture to be purified and for washing the cationic exchange matrix before the elution contains 20 mM MES and 1 mM EDTA.

12. A process according to claim 1 wherein the aqueous buffered solution for the elution from the cationic matrix contains 25 mM TRIS and 1 mM EDTA.

13. A process according to claim 1 wherein the aqueous buffered solution for the elution from the anionic matrix contains 25 mM TRIS, 100 mM NaCI and 1 mM EDTA.

14. A process according to claim 1 wherein the cationic exchange matrix is selected from cellulose-based, dextran-based, agarose-or cross-linked agarose-based, synthetic organic polymers-based and coated silica matrices-based cation exchangers, which Is optionally functionalized with carboxymethyl, sulfonate, sulfoethyl or sulfopropyl groups.

15. A process according to claim 14 wherein the cationic exchange matrix employed in step (a) is a cross-linked agarose based or synthetic organic polymers based cation exchanger, functionalized with sulfonate or sulfopropyl groups.

16. A process according to claim 1 wherein the anionic exchanger employed in step (b) is selected from a cellulose based, dextran based, agarose or cross-linked agarose based, synthetic organic polymers based and coated silica matrices based anion exchanger, functionalized with diethylaminoethy-1, quaternary aminomethyl, quatemary aminoethyl diethyl-(2-hydroxy-propyl) aminoethyl, triethylaminomethyl, triethylaminopropyl or poliethylene-imine groups.

17. A process according to claim 16 wherein the anionic exchanger employed in step (b) is a cross-linked agarose-based or synthetic organic polymers-based anion exchangers which is functionalized with a quaternary aminomethyl group.

* * * * *